US00PP35970P2

(12) United States Plant Patent
Crane

(10) Patent No.: US PP35,970 P2
(45) Date of Patent: Jul. 9, 2024

(54) APPLE TREE NAMED '102543s/2'

(50) Latin Name: ***Malus domestica* Mill.**
Varietal Denomination: 102543s/2

(71) Applicant: Prevar Limited, Hastings (NZ)

(72) Inventor: Barclay Crane, Spokane, WA (US)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 18/085,033

(22) Filed: Dec. 20, 2022

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875
See application file for complete search history.

*Primary Examiner* — Kent L Bell
(74) *Attorney, Agent, or Firm* — Michelle Bos Legal LLC

(57) ABSTRACT

A new and distinct apple tree named '102543s/2' notable for its fruit, which exhibits an attractive blush overcolor.

3 Drawing Sheets

Genus and species: *Malus domestica* Mill.
Variety denomination: '102543s/2'.

BRIEF DESCRIPTION OF THE VARIETY

A new apple tree named '102543s/2' was discovered near Quincy, Washington in 2016 as a spontaneous limb sport mutation of a 'PremA17' apple tree (U.S. Plant Pat. No. 22,546) growing in a cultivated orchard of 'PremA17' trees. One limb of the 'PremA17' tree bore fruit that exhibited an attractive blush color as compared to the other fruit on the tree. Asexual propagation by grafting was carried out in 2016 at Quincy, Washington. The variety has since been observed over a number of asexually propagated generations, and has been found to remain true to type.

'102543s/2' is distinguished from its parent 'PremA17' and from similar variety 'Gala' (U.S. Plant Pat. No. 3,637) by the characteristics set forth in Table 1 and Table 2 below.

TABLE 1

Comparison of '102543s/2' to 'PremA17'

| | '102543s/2' | 'PremA17' |
|---|---|---|
| Pattern of overcolor | Blush with very subtle striping | Stripe and blush |
| Overcolor | Red-purple 59A blush at stem end, fading to red 46A blush at calyx end | Red 45A stripe with red 47B blush |
| Intensity of overcolor | Moderate to intense | Moderate |
| Amount of overcolor | 75%+ of surface | 25% of surface |

TABLE 2

Comparison of '102543s/2' to 'Gala'

| | '102543s/2' | 'Gala' |
|---|---|---|
| Color pattern | Solid ground color with moderate to | Solid ground color with broadstriped |

TABLE 2-continued

Comparison of '102543s/2' to 'Gala'

| | '102543s/2' | 'Gala' |
|---|---|---|
| | intense blush and very subtle striped overcolor | and mottled overcolor |
| Flavor profile | Sweet, sub-acid | Sweet |

BRIEF DESCRIPTION OF THE PHOTOGRAPHS

The accompanying photographs were obtained in 2022 at Quincy, Washington. The trees depicted are five years old.

DETAILED BOTANICAL DESCRIPTION OF THE VARIETY

Figure 1:
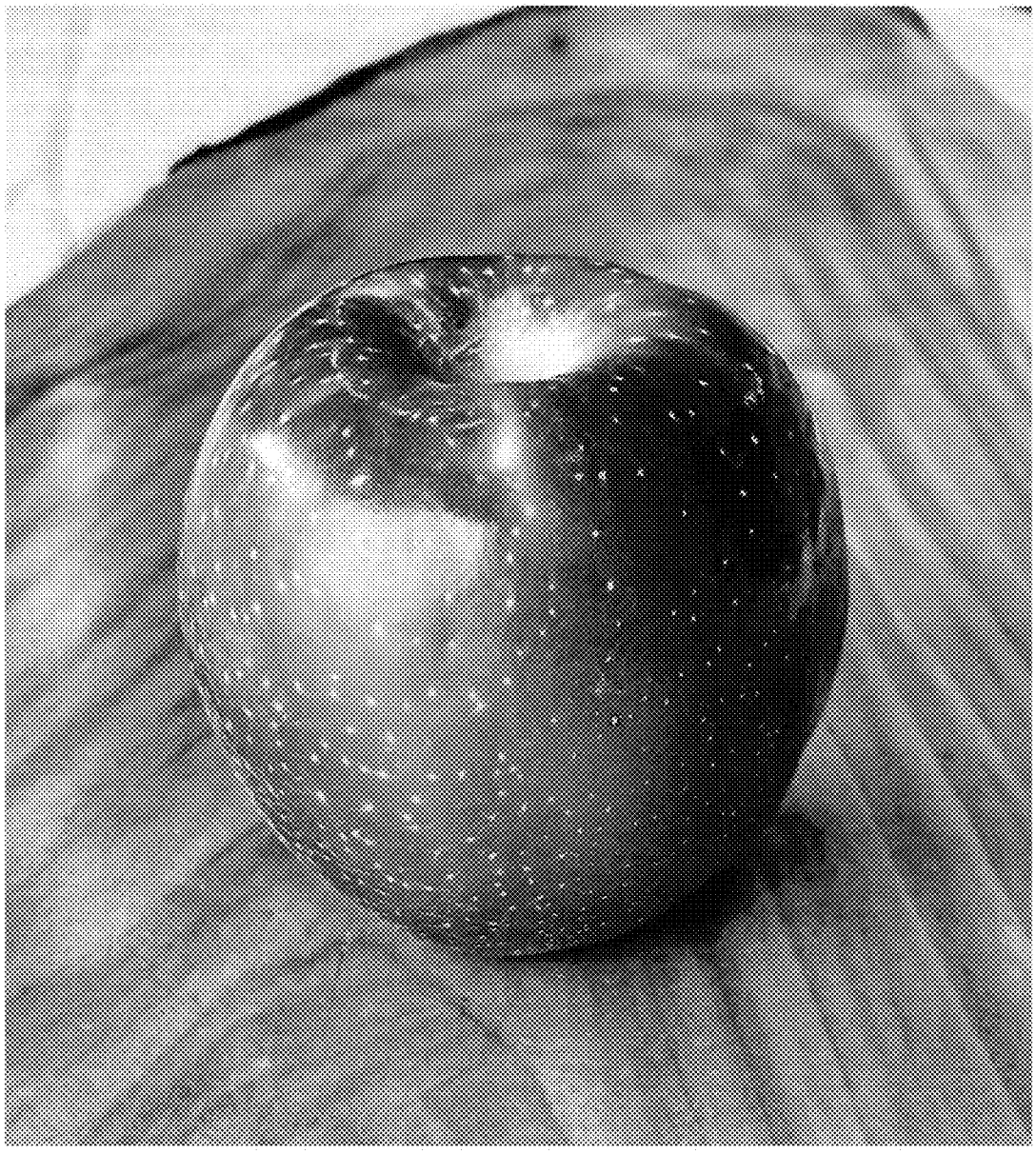
FIG. 1 shows a '102543s/2' apple.
Figure 2:
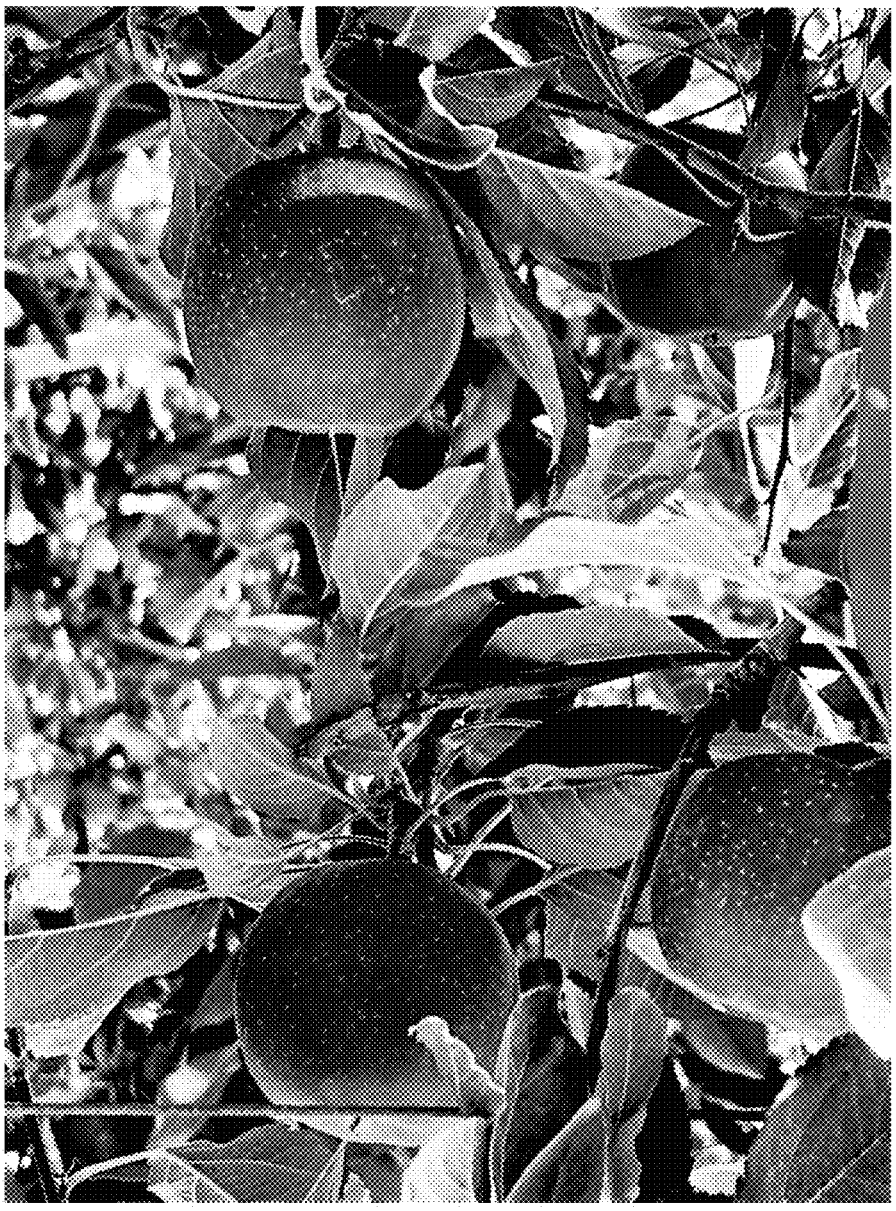
FIG. 2 shows leaves and fruit on a '102543s/2' apple tree.
Figure 3:
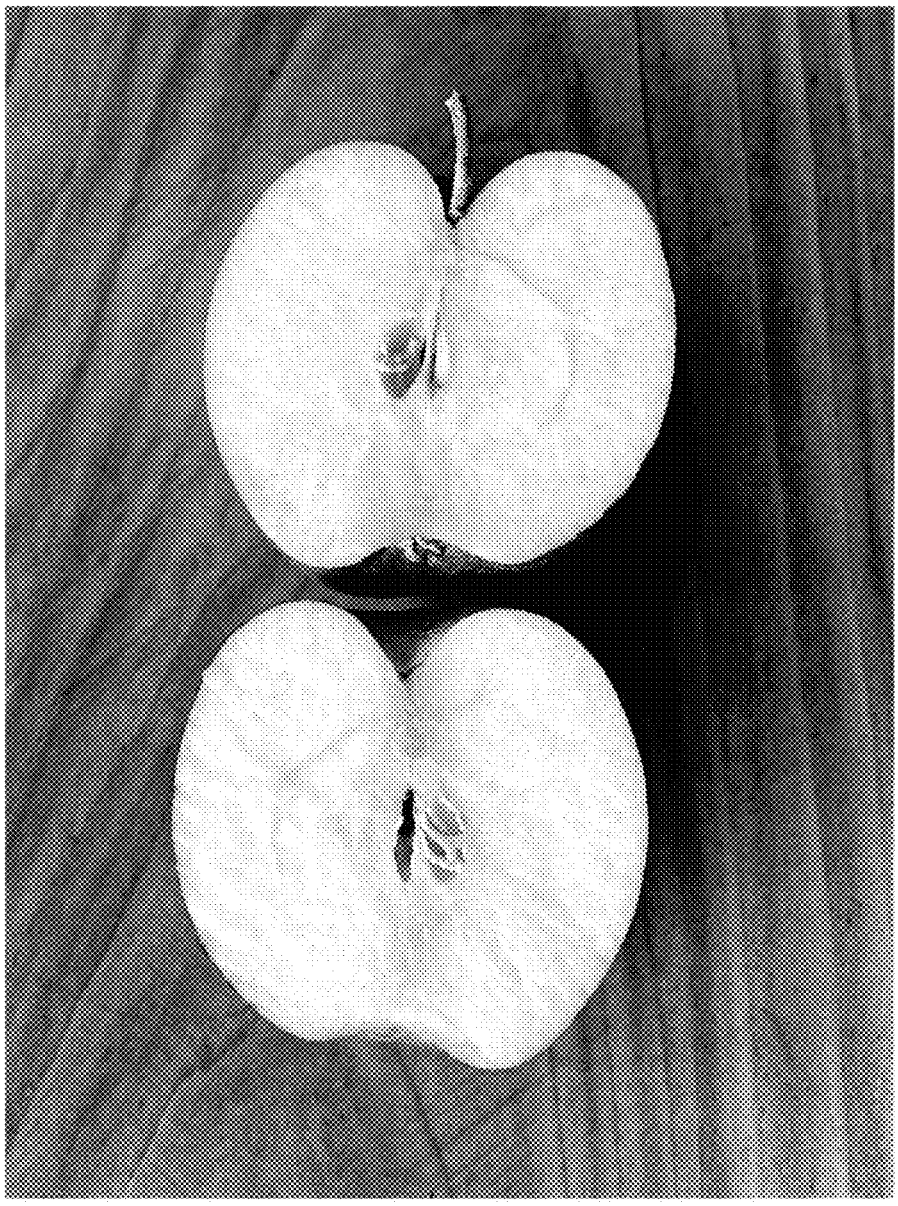
FIG. 3 shows a sectioned '102543s/2' apple.

The following detailed botanical description is based on observations of four-year-old trees growing on 'M9-337' rootstock (not patented), made during the 2022 growing season near Parker, Washington. The described trees are biaxial, grown on a V-trellis. All colors are described according to The Royal Horticultural Society Colour Chart (2001). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:

*Vigor*.—Semi-vigorous.

*Type*.—Columnar.

*Habit*.—Spreading.
*Spread of mature tree*.—About 0.9 m.
*Height*.—About 3.5 m.
*Bearing*.—Spurs and long shoots.
*Trunk diameter*.—6 cm at 30 cm above graft union.
*Bark texture*.—Semi-rough.
*Bark color*.—Brown N200D.
*Lenticel length*.—6 mm.
*Lenticel width*.—2 mm.
*Lenticel shape*.—Elongated.
*Lenticel color*.—Greyed-orange 165C.
*Lenticel density per* $cm^2$.—5 to 6.

Fruiting branches (1 m above graft union):
*Length*.—43 cm.
*Diameter*.—0.5 cm.
*Crotch angle*.—70°.
*Color*.—Brown N200D.
*Lenticel length*.—2 mm.
*Lenticel width*.—1 mm.
*Lenticel shape*.—Elongated.
*Lenticel color*.—White 155D.
*Lenticel density per* 10 $cm^2$.—8 to 10.

One-year-old shoot:
*Length*.—19 cm.
*Diameter*.—0.4 cm.
*Color*.—Brown 199A.
*Texture*.—Smooth.
*Internode length*.—3 cm to 4 cm.
*Lenticel length*.—1 mm.
*Lenticel width*.—0.5 mm.
*Lenticel shape*.—Elongated.
*Lenticel color*.—White 155A.
*Lenticel density per* 10 $cm^2$.—12 to 15.

Flowers buds at pre-balloon stage (Apr. 21, 2022):
*Quantity per spur*.—6.
*Bud shape*.—Globose to ovate.
*Apex shape*.—Rounded.
*Length*.—1 cm.
*Diameter*.—0.6 cm.
*Color*.—Red-purple N57B.

Flowers:
*Date of first bloom*.—April 25.
*Date of full bloom*.—April 28.
*Diameter of fully open flower*.—4 cm.

Petals:
*Relative position of petal margins*.—Not touching.
*Quantity per flower*.—5.
*Length*.—2 cm.
*Width*.—1.3 cm.
*Petal shape*.—Ovate.
*Apex shape*.—Rounded.
*Base shape*.—Cuneate.
*Margin*.—Entire.
*Color*.—Upper surface white N155A with red-purple 58D venation; lower surface white N155A with red-purple 58D near apex.
*Pistil length*.—1 cm.
*Pistil color*.—Green 142C.
*Style length*.—9 mm.
*Style color*.—Green 142C.
*Stigma diameter*.—1 mm.
*Stigma color*.—Green 142C.
*Ovary length*.—5 mm.
*Ovary color*.—Green 143B.
*Stamen quantity*.—15.
*Filament length*.—6 mm.
*Filament color*.—White 155A.
*Anther length*.—2 mm.
*Anther width*.—1 mm.
*Anther color*.—Yellow 4D.
*Presence of pollen*.—Present, scarce.
*Pollen color*.—Yellow 4D.

Pedicel:
*Length*.—2.5 cm.
*Diameter*.—1 mm.
*Color*.—Green 139D.
*Texture*.—Smooth.

Sepals:
*Quantity*.—5.
*Length*.—6 mm.
*Width*.—3 mm at base, tapering to a point.
*Shape*.—Lanceolate.
*Apex shape*.—Acute.
*Margin*.—Entire.
*Color*.—Upper surface Green — 142C.
*Color*.—Lower surface — Green 145C.

Leaves:
*Length*.—10 cm.
*Width*.—6.5 cm.
*Shape*.—Ovate.
*Apex*.—Acuminate.
*Base*.—Rounded, equilateral.
*Margin*.—Serrate.
*Venation*.—Reticulate.
*Color*.—Upper surface — Green 137A.
*Color*.—Lower surface — Yellow-green N148B.
*Color*.—Veins — Yellow-green 151C.
*Attitude in relation to shoot*.—Downward.

Petiole:
*Length*.—5 cm.
*Diameter*.—2 mm.
*Color*.—Yellow-green 151C.

Fruit:
*Diameter*.—9 cm.
*Height*.—8 cm.
*Weight*.—Average 260 g.
*Shape*.—Globose.
*Position of maximum diameter*.—Equator.
*Ribbing*.—Absent.
*Crowning at calyx end*.—Absent.
*Aperture of eye*.—Closed.
*Depth of eye basin*.—1.4 cm.
*Diameter of eye basin*.—2.0 cm.
*Stalk length*.—2.0 cm.
*Stalk diameter*.—4 mm.
*Stalk color*.—Yellow green 145C.
*Depth of stalk cavity*.—1.8 cm.
*Diameter of stalk cavity*.—1.0 cm.
*Russet around stalk cavity*.—Present.
*Bloom of skin*.—Absent.
*Greasiness of skin*.—Mild.
*Ground color of skin*.—Yellow-orange 20B.
*Over color of skin*.—Red-purple 59A blush at stem end, fading to red 46A blush at calyx end.
*Pattern of overcolor*.—Blush with very subtle striping visible.
*Intensity of overcolor*.—Moderate to intense.
*Amount of overcolor*.—75%+.
*Lenticel shape*.—Round and triangular.
*Lenticel diameter*.—1 mm to 2 mm.

*Lenticel density*.—Sparse on upper half, become near dense toward calyx end.
*Flesh color*.—White 158B.
*Flesh firmness*.—Firm, 9.5 kg/cm$^2$.
*Flesh texture*.—Crunchy, crisp.
*Juiciness*.—Moderately juicy.
*Brix*.—15°.

Seeds:

*Quantity per fruit*.—Few, 2 to 4.
*Length*.—8 mm.
*Width*.—7 mm.
*Shape*.—Ovate.
*Color*.—Greyed-orange 176A and 175D.
*Locule length*.—10 mm.
*Locule width*.—6 mm.
*Locules per fruit*.—6.
*Harvest date*.—Sep. 20, 2022, similar to 'PremA17'; second pick about one week later (2022 harvest was two weeks later than typical harvest).
*Number of picks*.—Two.
*Harvest yield*.—9 kg to 11 kg from trees described; yield will vary substantially depending on multiple factors.
*Disease/pest resistance*.—None observed.
*Disease/pest susceptibility*.—None noted.
*Market use*.—Fresh, juice processing.

The invention claimed is:

1. A new and distinct variety of apple tree named '102543s/2', substantially as illustrated and described herein.

* * * * *